United States Patent [19]

Taylor

[11] Patent Number: 5,028,468
[45] Date of Patent: Jul. 2, 1991

[54] SURGICAL MAT WITH DISPOSABLE COVER

[75] Inventor: Alfred R. Taylor, Aylesbury, England

[73] Assignee: Pandel, Inc., Catersville, Ga.

[21] Appl. No.: 413,180

[22] Filed: Sep. 27, 1989

[51] Int. Cl.⁵ .............................................. B32B 1/06
[52] U.S. Cl. ...................................... 428/71; 428/76; 428/192
[58] Field of Search ................... 428/40, 71, 76, 192; 15/215, 216

[56] References Cited

U.S. PATENT DOCUMENTS

| | | | |
|---|---|---|---|
| 1,236,694 | 8/1917 | Ellis | 428/76 |
| 1,787,453 | 1/1931 | Murray | 428/76 |
| 3,420,022 | 1/1969 | Brock | 428/76 |
| 3,526,564 | 9/1970 | Crawford | 428/71 |
| 4,624,877 | 11/1986 | Lea et al. | 428/71 |
| 4,910,280 | 3/1990 | Robbins | 428/71 |

*Primary Examiner*—Alexander S. Thomas
*Attorney, Agent, or Firm*—Richard P. Crowley

[57] ABSTRACT

A protective floor mat system which includes a surgical mat designed for use in an operating room environment and which system includes a disposable cover for the floor mat, the disposable cover comprising an envelope enclosure to enclose the floor mat during its use and which envelope comprises a disposable sheet material, which sheet material is impervious to the penetration of liquids, such as blood, urine, disinfectants and body fluids, thereby preventing the contamination of the floor mat during use and permitting the outer, disposable envelope to be discarded after use.

15 Claims, 1 Drawing Sheet

SURGICAL MAT WITH DISPOSABLE COVER

BACKGROUND OF THE INVENTION

Floor mats or runners are commonly employed to provide for cushioning and shock-absorbing covering surfaces for objects or people and in particular, floor mats have been employed as anti-fatigue mats in medical operating room environments. In particular, vinyl chloride floor mats composed of a vinyl chloride foam or solid layers or combinations thereof are often used as floor and surface coverings. Such floor mats, if desired, may include anti-static additives so that the mats may be employed in areas containing sensitive electronic equipment and to prevent the accumulation of static charges in medical environments. Such floor mats may also contain various anti-microbial agents to reduce or prevent the growth of bacteria. Floor mats have been proposed and used in medical environments, such as operating rooms, to provide a reduction, for example, up to 50% reduction, in the typical operating room floor hardness. Such floor mats have been provided as both non-disposable and disposable floor mats. Some floor mats are foam polyvinyl chloride floor mats which are constructed to lie flat and not to curl and to provide the same traction as a typical operating room floor. While such floor mats may be designed to be disposable, the floor mats do in effect increase hospital costs and particularly where such floor mats have a friction-type top surface, such as an embossed, granular or striated surface, which is difficult to clean with disinfectant solutions after becoming stained with blood, urine, disinfectant and body fluids from the operating room environment.

It is therefore desirable to provide for a more effective and disposable surgical mat system particularly for use in an operating room environment.

SUMMARY OF THE INVENTION

The invention relates to a protective floor mat system, particularly a surgical mat, having a disposable protective cover, and to the protective cover employed with the floor mat and to the method of protecting a cushioning mat from liquid contamination.

The invention relates to a protective floor mat system, such as a surgical floor mat system, protecting a cushioning mat, and more particularly, a floor mat, from contamination by liquid spillage in the environment in which the mat is being employed. Generally, this system is directed to the employment of floor mats used in medical environments, such as operating rooms, by surgeons, which mats are employed to provide a cushioning surface for the operating room personnel. Such floor mats are often exposed to spillage and contamination from blood, urine, disinfectant solutions and body fluids during use. These floor mats may be continually disinfected, but more generally are employed for a day and then discarded.

The invention comprises a protective floor mat system wherein the floor mat is composed of a resilient or particularly a foam material which is used in an environment in which the mat surface is subject to contamination by the spillage of liquids thereon, such as in an operating room environment, and which floor mat is of sufficient thickness and resiliency to reduce the fatigue of a user and which also comprises a envelope-type floor mat enclosure to enclose the floor mat and provide protection of the mat during use from liquid spillage in the environment in which the mat is used. The envelope-type enclosure comprises a sterile, disposable sheet material of low cost which forms an envelope-type enclosure in which the floor mat may be placed prior to use. The sheet material of the envelope should be designed to be impervious to liquid spillage and contamination and also of low cost so that the contaminated envelope may be removed and disposed of after use. The envelope may be composed of a disposable and inexpensive sheet material which is typically employed for example in medical environments and operating rooms, such as the nonwoven type sheet material used in operating room clothing, coverings and boots employed by operating room personnel.

The disposable sheet material employed for the enclosure comprises in one embodiment a nonwoven, fibrous layer, such as of polypropylene or polyester fiber or a combination thereof, such as United Paper Mills Ltd.'s Reg. 760 or 761 blue, non-woven sheet material with a range of about 65 to 90 gm/m$^2$, which is capable of some absorption of the liquid into the layer as a top surface layer for the envelope enclosure employed about the floor mat, and an inner, liquid-impervious plastic layer, such as a polyolefin layer, like a polyethylene or polypropylene layer, to prevent the penetration of the liquid materials into the interior of the enclosure.

In another embodiment, the disposable sheet material for the mat closure may comprise one or more layers of a thin, solid, polymeric sheet material, e.g. such as a polyolefin, like polyethylene or polypropylene or a vinyl polymer like polyvinyl chloride which may have the edges sealed by an adhesive or more particularly by heat or sonic welding to ensure a stronger edge and flap sealed closure for the mat. The polymeric material should be nonabsorbent and may have the surface treated or embossed to be skid resistant and the polymeric material made antistatic.

The protective floor mat system also includes a means to seal the enclosure means after enclosing the floor mat therein to prevent the liquid contamination from reaching the floor mat, and generally, such means to seal comprises an adhesive about or adjacent the flap of the envelope enclosure or an adhesive tape used to seal effectively the enclosure or adhesives or hot welding of the seams where applicable.

The protective floor mat system thus provides for the safeguarding of the floor mat in use yet permits the floor mat to act as an anti-friction, anti-static, anti-microbial and anti-fatigue floor mat and permits the continuous use of the floor mat, subject to disinfectant from time to time, by the use of a disposable envelope to enclose the floor during its actual usage. In use, the floor mat is placed in the envelope enclosure, the envelope enclosure effectively sealed and then the envelope with the enclosed floor mat placed on the floor or surface on which the operating room personnel stand. After use, the seal is removed from the enclosure and the contaminated enclosure is then removed and discarded as medical waste. The floor mat may be cleaned with a disinfectant and then reintroduced into another envelope enclosure. This system permits the continual use of the floor mat and provides an effective means to protect the floor mat during use from gross contamination.

The floor or surface covering mat employed within the envelope enclosure can be composed of any type of a rubber or plastic type material, but more typically comprises a vinyl chloride, closed cell foam floor mat of suitable size and thickness to act as a floor mat and typically ranging from about 2'×3' or 3'×5' size or even as a runner ranging in thickness from about one-quarter to one-half inch in thickness which optionally may be colored to be a surgical type blue or green to be in color conformance with the operating room in which it is employed. Generally, the foam-type mat is of a closed cell or partially closed cell foam to provide a good cushion and has a foam density ranging from about 15 to 30 pounds per square foot, such as for example from 18 to 24 pounds per square foot. Generally, such vinyl foam mats are prepared by casting a thin layer of an expandable liquid vinyl plastisol composition onto a releasable surface and then heating the vinyl plastisol layer to expand and fuse the plastisol to provide a flexible cushion foam material.

If desired, the foam material may include therein a dimensionally stable sheet material, such as for example, a glass fiber scrim material therein, to aid in the prevention of edge curling of the floor mat. In addition, the floor mat may also contain minor, but effective amounts of an anti-static agent to reduce the electrical conductivity of the mat, and therefore, avoid the accumulation of electrical charges in use by the employment of various conventional anti-static agents, such as quaternary ammonium salts, carbon black particles and fatty acid and glycol type additives. Also, the floor mat may contain anti-microbial agents to reduce or prevent the growth of bacteria or fungi in use which antibacterial agent may comprise, for example, a pyridinium halide, such as cetylpyridinium chloride, as well as quaternary ammonium compounds and other conventional type anti-microbial agents. Further, if desired, the floor mat, as well as the envelope, either alone or in combination may be subject to irradiation, disinfectants, liquids or gases or other techniques to render each of the components sterile and suitable for use in an operating room environment.

In one embodiment, the floor mat may comprise a polyvinyl chloride foam floor mat wherein the surface may be embossed, striated or have a grain-type texture to impart an anti-skid surface to the floor mat. However, where employed in a medical embodiment optionally the surface of the floor mat should be smooth which makes cleaning of the surface of the floor mat more effective after removal from the disposable envelope. Thus, in one preferred embodiment, the floor mat contains smooth surfaces on each side to enhance the disinfecting and cleaning of the floor mat after use. The floor mat usually has closed or crimped edges, that is, the edges of the floor mat are sealed so as to prevent liquid contamination, and more particularly, the floor mat may have the top and bottom or both surfaces coated with a thin layer of a protective polymer, such as an aqueous, thermoplastic urethane polymer so as to seal further the top and bottom surfaces of the vinyl foam floor mat with a thin layer, such as 0.3 to 3 mils of a urethane polymer coating.

The enclosure used to enclose the floor mat may comprise a wide variety of shapes and forms, but typically may comprise an envelope-type enclosure formed of a liquid-impervious sheet material suitable for use in the operating room environment. More particularly, the envelope typically comprises a flap-type envelope wherein the flap at one short end is adapted to be sealed adhesively against the body of the envelope to provide an effective seal with the floor mat therein. The sheet material is composed of an absorbent, fibrous face and a thin, liquid-impervious, plastic interior coating and is folded over to form a fold at one end, and then the other opposing edges are either sewn or heat sealed or otherwise sealed together with the other end forming a flap. The flap edges are coated with an adhesive with a removable tape so that the tape may be peeled off, and the exposed adhesive employed to then seal the flap.

The vinyl foam, edge sealed, smooth surface floor mat is particularly adapted as a surgical floor mat, particularly as a urethane-coated mat, which is resistant to body fluids, disinfectants and most chemicals and which urethane coating resists slippage by users while the anti-static additive provides for a static dissipative type mat which is non-sparking and designed to minimize static build up on personnel, while the floor mat is also anti-microbial formulated for effective resistance to bacteria, mold and fungi as well as providing an effective cushioning.

The protective floor system and the protective enclosure will be described for the purposes of illustration only in connection with the surgical floor mat containing a protective, disposable, inexpensive enclosure for use in a medical environment. However, it is recognized that the protective floor mat system may be employed in a wide variety of environments wherein a reusable floor mat or other mat as a surface covering may need to be protected from use environment. The protective envelope may be used in electronic clean rooms and in other areas where cleanliness is desirable. Therefore, the invention will be described for the purposes of illustration only in connection with the surgical floor mat system; however, it is recognized that various changes, modifications, improvements and additions may be made by those persons skilled in the art, all falling within the spirit and the scope of the described embodiments.

DESCRIPTION OF THE EMBODIMENTS

Figure 1:
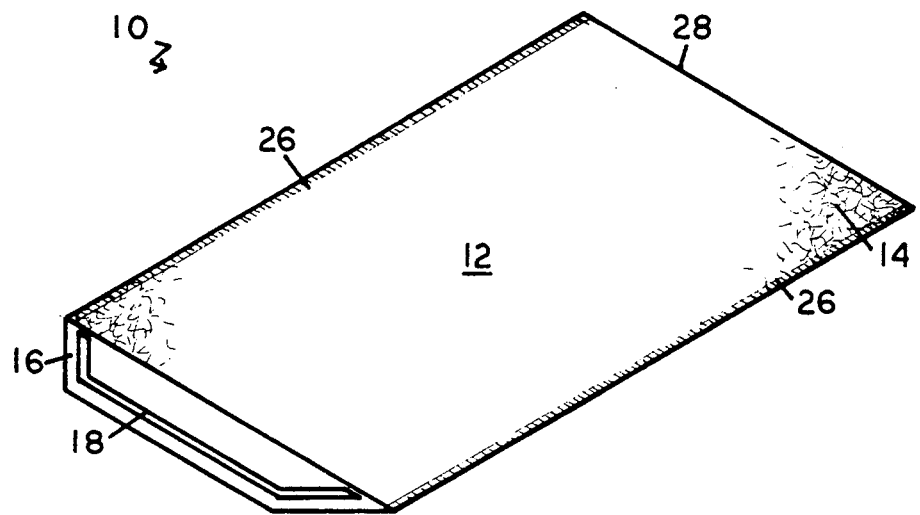
FIG. 1 is a perspective, illustrative view of a protective envelope employed in the protective floor mat system.
Figure 2:
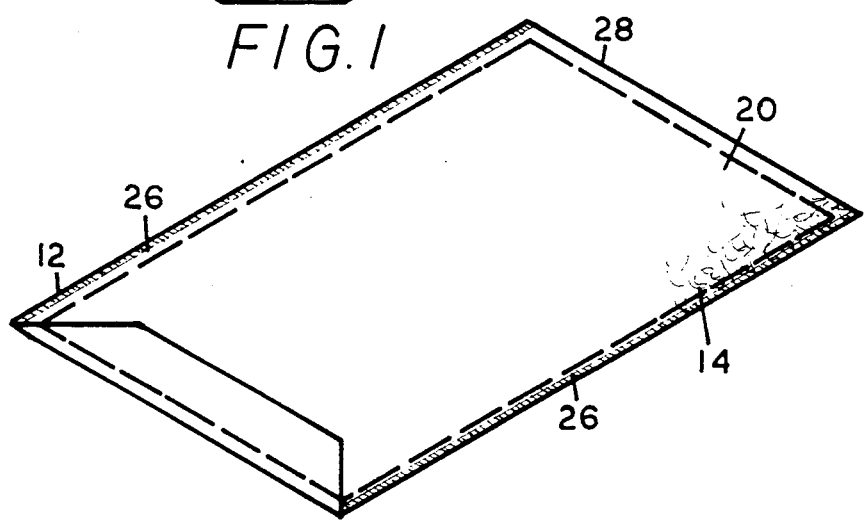
FIG. 2 is a perspective, illustrative view of a protective floor mat system wherein a surgical floor mat is enclosed in a protective envelope.

The drawings show a protective floor mat system 10 comprising an envelope 12 having an exterior surface composed of nonwoven, absorbent, polyester type fibers layer 14 and an internal, thin, plastic, polyethylene-coated layer 16 with the flap of the envelope having a tape 18 which covers a seal-type adhesive, the tape adapted be peeled off so that the flap may be secured by the underlying adhesive to the body of the envelope 12 as illustrated more particularly in FIG. 2. The envelope 12 is composed of a liquid-impervious sheet material composed of the layers 14 and 16 and is formed by folding over the sheet material having a folded edge 28 with the adjoining edges 26 on either side illustrated as sewn together to seal the enclosure.

As illustrated in FIG. 2, the protective floor mat system is shown wherein a surgical floor mat of, for example, 3'×2½' and ⅜" thickness composed of a closed cell, polyvinyl foam with smooth surface 24 and urethane coated on both surfaces and with all the side edges 22 crimped sealed, and the floor mat shown in dotted lines enclosed and sealed in the envelope 12.

Figure 3:
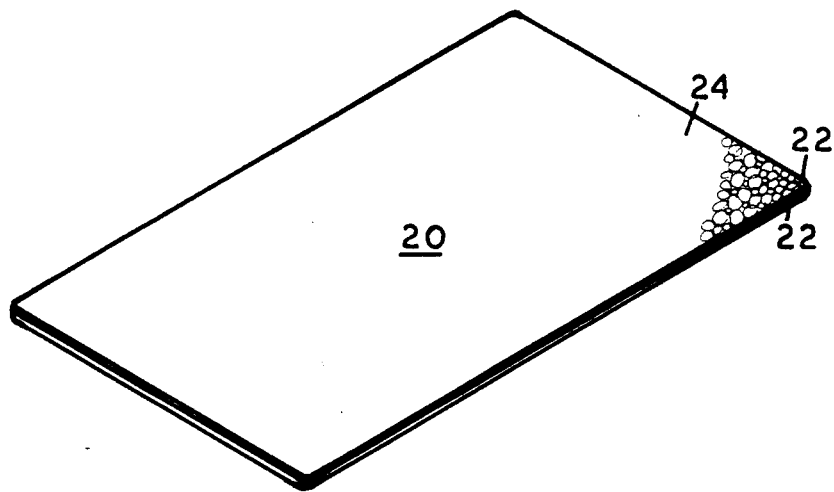
FIG. 3 is a perspective, illustrative view of a surgical floor mat employed in the protective floor mat system of the invention.

FIG. 3 illustrates the resilient floor mat 20 and shows the tape and heat sealed edges 22 with a urethane coating 24 on the top smooth surface. The surgical floor mat system provides for a reusable, resilient floor mat 20 enclosed within a sealable envelope 12 for use in an operating room environment and when in use the sealed floor mat 20 in the envelope 12 is placed so that the flap of the envelope is adjacent the floor surface. After use, the flap is opened, the floor mat removed, disinfected and placed in another protective envelope, while the used protective envelope with the contamination is then discarded.

What is claimed is:

1. A protective floor mat system for protecting a cushioning floor mat from contamination by liquid spillage in the environment in which the mat is used, which system comprises in combination:
   a) a separate, reusable, insertable and removable floor mat composed of a sheet material for use in an environment in which the mat is subject to contamination by the spillage of liquid thereon, the floor mat of sufficient thickness and resiliency to reduce the fatigue of a user;
   b) an envelope mat enclosure means into which the floor mat may be separately inserted and removed for re-use to enclose the floor mat and provide protection from liquid spillage which enclosure means comprises a disposable sheet material forming an envelope in which the mat is placed, wherein the disposable sheet material comprises a fibrous exterior surface layer to aid in the absorption of the spilled layer and a thin, liquid, impervious plastic interior surface layer, the sheet material impervious to liquid spillage to prevent the penetration of spilled liquid onto the enclosed mat, the envelope subject to disposal after use and removal of the floor mat; and
   c) means to seal the enclosure means after enclosing the mat therein.

2. The system of claim 1 wherein the floor mat is comprised of a foam polyvinyl chloride material.

3. The system of claim 2 wherein the floor mat contains a thin urethane polymer coating layer to resist the penetration of spilled liquids.

4. The system of claim 1 wherein the floor mat contains an antistatic agent to minimize static buildup.

5. The system of claim 1 wherein the floor mat contains an antimicrobial agent to increase the resistance of the floor mat to bacteria, fungi and mold.

6. The system of claim 1 wherein the floor mat is characterized by smooth top and back surfaces.

7. The system of claim 1 wherein the floor mat is characterized by tapered sealed edges about the periphery of the floor mat.

8. The system of claim 1 wherein the disposable sheet material of the enclosure means comprises an exterior, nonwoven, absorbent fibrous layer and a polyolefin interior layer.

9. The system of claim 1 wherein the enclosure means comprises a folded sheet material with opposing edges sealed and one edge with a flap open for the insertion of the floor mat in use.

10. The system of claim 1 wherein the floor mat and the enclosure means are sterilized and the system is adapted for use as a surgical floor mat in a medical operating room environment.

11. The system of claim 1 wherein the means to seal the enclosure means comprises an adhesive tape.

12. The system of claim 1 wherein the enclosure means comprises a thin, disposable, polymeric sheet material.

13. The system of claim 12 wherein the polymer sheet material comprises a polyvinyl chloride polymer.

14. The system of claim 1 wherein the disposable sheet material comprises a top surface layer of a polypropylene or polyester fiber to absorb spilled liquid and an inner polyolefin, liquid-impervious layer.

15. The system of claim 14 wherein the enclosure means comprises a generally rectangular envelope of the disposable sheet material, the disposable sheet material sealed along three edges thereof and having an opening at the one end with an adhesively sealable flap extending at the one end whereby after insertion of the floor mat the flap may be folded over and sealed against the external surface of the disposable sheet material.

* * * * *